(12) United States Patent
Tribble et al.

(10) Patent No.: US 11,096,867 B2
(45) Date of Patent: Aug. 24, 2021

(54) RECONSTITUTION DEVICE FOR IV FLUIDS AND METHOD OF USE

(71) Applicant: CareFusion 303, Inc., San Diego, CA (US)

(72) Inventors: Dennis Anthony Tribble, Ormond Beach, FL (US); Thomas Utech, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 16/807,091

(22) Filed: Mar. 2, 2020

(65) Prior Publication Data

US 2020/0197261 A1 Jun. 25, 2020

Related U.S. Application Data

(62) Division of application No. 15/214,325, filed on Jul. 19, 2016, now Pat. No. 10,576,018.

(51) Int. Cl.
*A61J 1/20* (2006.01)
*A61J 1/14* (2006.01)
(Continued)

(52) U.S. Cl.
CPC ............ *A61J 1/2048* (2015.05); *A61J 1/10* (2013.01); *A61J 1/1475* (2013.01); *A61J 1/1493* (2013.01);
(Continued)

(58) Field of Classification Search
CPC .......... A61J 1/2048; A61J 1/10; A61J 1/1475; A61J 1/1493; A61J 1/20; A61J 2205/30;
(Continued)

(56) References Cited

U.S. PATENT DOCUMENTS

| 4,559,053 A | 12/1985 | Porges |
|---|---|---|
| 9,987,655 B2 | 6/2018 | deVilliers |

(Continued)

FOREIGN PATENT DOCUMENTS

| CN | 1046466 A | 10/1990 |
|---|---|---|
| CN | 101501693 A | 8/2009 |

(Continued)

OTHER PUBLICATIONS

Chinese Office Action for Application No. 201780057281.6, dated Jan. 7, 2021, 8 pages including translation.

(Continued)

*Primary Examiner* — Michael Collins
(74) *Attorney, Agent, or Firm* — Morgan, Lewis & Bockius LLP

(57) ABSTRACT

A system is provided for storage and reconstitution of IV solutions. The system may include one or more storage and reconstitution devices each configured to store and manipulate IV solution containers containing IV solutions in crystalline form that include hydration chemicals and therapeutic drugs. Crystalline hydration chemicals may include crystalline salts and sugars. The containers may be dimensionally precise enough for mechanical manipulation and configured such that sharp objects such as needles are not needed for fluid delivery to or from the container. Each storage and reconstitution device may store stacked containers and may include components for retrieval of a container from the storage and for reconstitution of the contents therein using a sterile water source within the device. IV doses may be manufactured, under appropriate standards, that can be mechanically reconstituted to produce high-quality doses in real time on the patient care unit or in the pharmacy.

20 Claims, 8 Drawing Sheets

(51) Int. Cl.
*A61J 1/10* (2006.01)
*B65C 3/26* (2006.01)
*B65D 21/02* (2006.01)

(52) U.S. Cl.
CPC .............. *A61J 1/20* (2013.01); *B65C 3/26* (2013.01); *B65D 21/0209* (2013.01); *A61J 2205/10* (2013.01); *A61J 2205/30* (2013.01); *A61J 2205/60* (2013.01)

(58) Field of Classification Search
CPC ..... A61J 2205/10; A61J 2205/60; B65C 3/26; B65D 21/0209; B65D 81/3222
USPC ................................. 700/235, 239; 222/129
See application file for complete search history.

(56) References Cited

U.S. PATENT DOCUMENTS

| | | | |
|---|---|---|---|
| 10,347,374 B2 * | 7/2019 | Tribble | ............ G16H 70/40 |
| 10,576,018 B2 * | 3/2020 | Tribble | ................ A61J 1/10 |
| 2004/0004037 A1 | 1/2004 | Herron | |
| 2012/0063973 A1 | 3/2012 | Ang | |
| 2014/0031976 A1 | 1/2014 | Reinhardt et al. | |
| 2014/0346071 A1 | 11/2014 | Genosar | |
| 2015/0045289 A1 | 2/2015 | West | |

FOREIGN PATENT DOCUMENTS

| | | |
|---|---|---|
| CN | 101528910 A | 9/2009 |
| CN | 102131486 A | 7/2011 |
| CN | 104334467 A | 2/2015 |
| EP | 2055767 | 5/2009 |
| EP | 2298269 | 3/2011 |
| WO | WO-2004/033954 | 4/2004 |
| WO | WO-2006124211 | 11/2006 |
| WO | WO-2012158973 A3 | 11/2012 |
| WO | WO-2013/183986 | 12/2013 |

OTHER PUBLICATIONS

Invitation to Pay Additional Fees from PCT/US2017/039565, dated Sep. 22, 2017, 4 pages.
International Search Report and Written Opinion for Application No. PCT/US2017/039565, dated Dec. 20, 2017, 16 pages.
Extended European Search Report for Application No. 20175447.0, dated Jul. 21, 2020, 8 pages.

* cited by examiner

RECONSTITUTION DEVICE FOR IV FLUIDS AND METHOD OF USE

CROSS-REFERENCE TO RELATED APPLICATIONS

This application is a divisional of U.S. patent application Ser. No. 15/214,325, filed Jul. 19, 2016, now U.S. Pat. No. 10,576,018, issued Mar. 3, 2020, which is hereby incorporated by reference herein in its entirety.

TECHNICAL FIELD

The present disclosure generally relates to reconstitution for medical fluids and, more particularly, to intravenous fluid containers and systems and methods for storage, reconstitution of doses within, and tracking of the intravenous fluid containers.

BACKGROUND

Intravenous (IV) solutions are typically sterile liquid doses produced in containers varying in size from 50 mL to 1000 mL. These IV solutions may be basic chemical solutions used for hydration, the most common being 0.9% Sodium Chloride (sometimes referred to as saline or normal saline), and Dextrose 5% in Water (D5W). Many containers for these solutions are plastic bags, plastic bottles, or glass bottles. These solutions are currently manufactured in fluid form, delivered to healthcare institutions, and stored there for use. They are used in the U.S. alone in quantities of millions.

The state of the art described above can have, in various circumstances, one or more drawbacks, excess costs, and/or complications. For example, current IV solutions are commonly stored, shipped, and used as complete fluid products, which means that they require immense amounts of storage space, are heavy, and are expensive to ship.

Additionally, many commonly used drugs are not chemically stable in a solution, with the result that doses containing these drugs cannot easily be manufactured with sufficient shelf life to survive the quality/regulatory systems required for their manufacture, much less the time required to get them into, and through the supply chain to their end-users. Conventional approaches to this chemical stability problem include: (a) manual preparation in healthcare facilities—i.e., the drugs must be liquefied and injected into liquid IV solutions prior to administration, (b) special adapters to IV fluid containers that permit a vial of the drug to be attached to an IV solution for activation just before use (e.g., the Baxter MiniBag Plus®, or Hospira ADDvantage®), and (c) freezing, in which, when the drug chemistry permits, the IV dose is prepared and frozen to limit degradation. However, each of these conventional approaches can have, if care is not taken, one or more drawbacks.

In the case of manual preparation, the preparation can be hazardous both due to human error and due to contamination of the preparation. Manual preparation can also be labor-intensive, highly regulated, and require special facilities to ensure sterility and potency. Such manual preparation is, perforce, centralized in the pharmacy, which limits the pace at which doses can be prepared and delivered for patient use.

In the case of special adapter containers, the IV solutions add cost and the ingredients must be physically attached to the bag by a caregiver, the ingredients must be activated at run time—i.e., the caregiver must attach the vial to the IV solution container, activate it, move fluid from the IV solution container to the vial, dissolve the contents of the vial, and move the dissolved contents back to the IV solution container. If care is not taken, there can be a 2-3% failure-to-activate rate with conventional special adapter containers. Moreover, with special adapter containers, the number of different types of vials that can be delivered this way is small because many vials cannot be used with the special adapter and drugs delivered in glass ampules also cannot be delivered in this way.

In the case of freezing, special supply chain equipment and processes are commonly required to ensure the frozen state is maintained during storage and delivery, the doses must be stored frozen until needed and then thawed, thawing can be messy and requires additional space and equipment (e.g., for management of condensation), and, once thawed, the pharmacy is required to relabel each dose with new expiration dating based on the date of thawing.

Accordingly, improved systems and methods for providing IV solutions would be desirable.

SUMMARY

Systems, methods, devices, and containers for reconstitution of crystalline contents of an intravenous (IV) solution dose are provided. For example, systems including one or more reconstitution devices for IV fluids and one or more IV solution containers for use therein are described herein, along with various associated reconstitution methods. An IV solution container may be provided with crystalline contents of an IV solution dose. The crystalline content may be reconstituted, by the reconstitution device, with sterile water just before injection to a patient. The reconstitution device may be a storage and reconstitution device with components for storing the IV solution containers with the crystalline contents, reconstituting the crystalline contents on demand, and providing appropriate labeling, and documentation for, the containers upon reconstitution.

In accordance with an embodiment, a stackable, machine-manipulable container is provided that includes: at least one crystalline hydration chemical; at least one crystalline therapeutic drug; a first port configured to receive sterile water for reconstitution of the at least one crystalline hydration chemical and the at least one crystalline therapeutic drug; and a second port configured to receive an intravenous set connector for delivery of a medical fluid formed from the at least one crystalline hydration chemical, the at least one crystalline therapeutic drug, and the sterile water.

In accordance with another embodiment, a storage and reconstitution device is provided that includes: a storage region configured to store a plurality of stacked, machine-manipulable containers, each container including at least one crystalline hydration chemical and at least one crystalline therapeutic drug; a replaceable sterile water reservoir; and robotic components configured to: move at least one of the plurality of stacked, machine-manipulable containers from the storage region to a connector fluidly coupled to the replaceable sterile water reservoir, add sterile water from the replaceable sterile water reservoir to the at least one of the plurality of stacked, machine-manipulable containers, agitate the at least one of the plurality of stacked, machine-manipulable containers, verify reconstitution of the at least one crystalline hydration chemical and at least one crystalline therapeutic drug within the at least one of the plurality of stacked, machine-manipulable containers, label the at least one of the plurality of stacked, machine-manipulable containers, store tracking information for the at least one of the plurality of stacked, machine-manipulable containers, and provide caregiver access to the at least one of the plurality of stacked, machine-manipulable containers.

In accordance with another embodiment, a system is provided that includes: a first storage and reconstitution device at a first location; and a second storage and reconstitution device at a second location, in which each of the first and second storage and reconstitution devices includes: a storage region configured to store a plurality of stacked, machine-manipulable containers, each container including at least one crystalline hydration chemical and at least one crystalline therapeutic drug; a replaceable sterile water reservoir; and robotic components configured to: move at least one of the plurality of stacked, machine-manipulable containers from the storage region to a connector fluidly coupled to the replaceable sterile water reservoir, add sterile water from the replaceable sterile water reservoir to the at least one of the plurality of stacked, machine-manipulable containers, agitate the at least one of the plurality of stacked, machine-manipulable containers, verify reconstitution of the at least one crystalline hydration chemical and at least one crystalline therapeutic drug within the at least one of the plurality of stacked, machine-manipulable containers, label the at least one of the plurality of stacked, machine-manipulable containers, store tracking information for the at least one of the plurality of stacked, machine-manipulable containers, and provide caregiver access to the at least one of the plurality of stacked, machine-manipulable containers.

In some embodiments, the system may include a control system communicatively coupled via a network to the first and second reconstitution devices and configured to push dose orders from clinicians to the first or second storage and reconstitution devices based at least in part on known contents of the stacked, machine manipulable containers stored therein.

In accordance with another embodiment, a method is provided that includes storing a plurality of stacked, machine-manipulable containers in a storage region of a storage and reconstitution device, each container including at least one crystalline hydration chemical; moving, with robotic components of the storage and reconstitution device, at least one of the plurality of stacked, machine-manipulable containers from the storage region to a connector of the storage and reconstitution device, the connector being fluidly coupled to a sterile water reservoir of the storage and reconstitution device; adding sterile water from the replaceable sterile water reservoir to the at least one of the plurality of stacked, machine-manipulable containers; agitating the at least one of the plurality of stacked, machine-manipulable containers; verifying reconstitution of the at least one crystalline hydration chemical within the at least one of the plurality of stacked, machine-manipulable containers; labeling the at least one of the plurality of stacked, machine-manipulable containers; storing tracking information for the at least one of the plurality of stacked, machine-manipulable containers; and providing caregiver access to the at least one of the plurality of stacked, machine-manipulable containers. Providing the caregiver access to the at least one of the plurality of stacked, machine-manipulable containers may include moving the at least one of the plurality of stacked, machine-manipulable containers to an access port of the storage and reconstitution device with the robotic components.

It should be appreciated that the embodiments described above are merely illustrative. In various other embodiments, a stackable, machine-manipulable container may be provided that includes one or more one crystalline hydration chemicals (e.g., in various suitable amounts and concentrations) without any crystalline therapeutic drugs. For example, in one illustrative scenario, a stackable, machine-manipulable container may be provided that contains crystalline Sodium Chloride in a quantity that, when reconstituted by the addition of sterile water (e.g., one liter of sterile water) into the stackable, machine-manipulable container, generates one liter of 0.9% Sodium Chloride. In this way, the efficiency of transporting and storing of one of the most commonly infused IV solutions (i.e., 1000 mL of 0.9% Sodium Chloride) can be greatly enhanced by eliminating the need to transport and store the fluid component of the solution.

In another illustrative scenario, a stackable, machine-manipulable container may be provided that contains crystalline Dextrose in a quantity that, when reconstituted by the addition of sterile water (e.g., 500 mL of sterile water) into the stackable, machine-manipulable container, generates 5% Dextrose in Water 500 mL.

More generally, in various embodiments, stackable, machine-manipulable containers may be provided that contain only crystalline hydration chemicals or that contain a combination of crystalline hydration chemicals and one or more crystalline therapeutic drug(s). For example, in another illustrative scenario, a stackable, machine-manipulable container may be provided that contains crystalline Dextrose and crystalline Dopamine in respective quantities that, when reconstituted by the addition of sterile water into the stackable, machine-manipulable container, generate an infusable dose of Dopamine 50 mg in 5% Dextrose in Water.

In accordance with another embodiment, a storage and reconstitution device is provided that includes: a storage region configured to store a plurality of stacked, machine-manipulable containers, each container including at least one crystalline hydration chemical; a replaceable sterile water reservoir; and robotic components configured to: move at least one of the plurality of stacked, machine-manipulable containers from the storage region to a connector fluidly coupled to the replaceable sterile water reservoir, add sterile water from the replaceable sterile water reservoir to the at least one of the plurality of stacked, machine-manipulable containers, agitate the at least one of the plurality of stacked, machine-manipulable containers, verify reconstitution of the at least one crystalline hydration chemical within the at least one of the plurality of stacked, machine-manipulable containers, label the at least one of the plurality of stacked, machine-manipulable containers, store tracking information for the at least one of the plurality of stacked, machine-manipulable containers, and provide caregiver access to the at least one of the plurality of stacked, machine-manipulable containers.

In accordance with another embodiment, a container is provided that includes a housing, including: a stackable, machine-manipulable rigid portion; and an expandable membrane sealingly attached to the stackable, machine-manipulable rigid portion to form an internal volume within the housing, the internal volume configured to store at least one crystalline hydration chemical and at least one crystalline therapeutic drug; a first port in the housing, the first port configured to receive sterile water for reconstitution of the at least one crystalline hydration chemical and the at least one crystalline therapeutic drug; and a second port in the housing, the second port configured to receive an intravenous set connector for delivery of a medical fluid formed from the at least one crystalline hydration chemical, the at least one crystalline therapeutic drug, and the sterile water.

In accordance with another embodiment, a storage and reconstitution device is provided that includes: a storage region configured to store a plurality of stacked, machine-manipulable containers, each container including at least one crystalline hydration chemical; a sterile water reservoir; and robotic components configured to: move at least one of the plurality of stacked, machine-manipulable containers from the storage region to a connector fluidly coupled to the sterile water reservoir, add sterile water from the sterile water reservoir to the at least one of the plurality of stacked, machine-manipulable containers, agitate the at least one of the plurality of stacked, machine-manipulable containers, verify reconstitution of the at least one crystalline hydration chemical within the at least one of the plurality of stacked, machine-manipulable containers, label the at least one of the plurality of stacked, machine-manipulable containers, and store tracking information for the at least one of the plurality of stacked, machine-manipulable containers.

In accordance with another embodiment, a system is provided that includes: a first storage and reconstitution device at a first location; a second storage and reconstitution device at a second location, in which each of the first and second storage and reconstitution devices includes: a storage region configured to store a plurality of stacked, machine-manipulable containers, each container including at least one crystalline hydration chemical and at least one crystalline therapeutic drug; a sterile water reservoir; and robotic components configured to: move at least one of the plurality of stacked, machine-manipulable containers from the storage region to a connector fluidly coupled to the sterile water reservoir, add sterile water from the sterile water reservoir to the at least one of the plurality of stacked, machine-manipulable containers, agitate the at least one of the plurality of stacked, machine-manipulable containers, and verify reconstitution of the at least one crystalline hydration chemical and at least one crystalline therapeutic drug within the at least one of the plurality of stacked, machine-manipulable containers; and a control system communicatively coupled via a network to the first and second storage and reconstitution devices and configured to push dose orders from clinicians to the first or second storage and reconstitution devices based at least in part on known contents of the stacked, machine manipulable containers stored therein.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
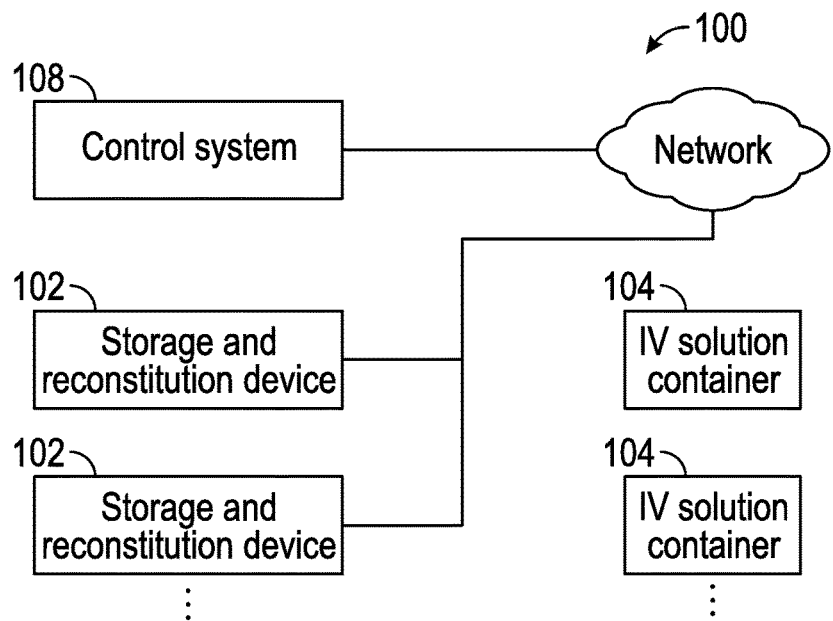
FIG. 1 illustrates a block diagram of an exemplary embodiment of an intravenous fluid storage and reconstitution system in accordance with aspects of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

IV solutions are sterile aqueous fluids containing sufficient salt or sugar content to have their osmolality approximate that of normal human serum. If solutions are too concentrated (i.e., if the solution has too high an osmolality), they withdraw fluid from blood cells and the cells lining the veins and essentially chemically burn the cells. If solutions are too dilute (e.g., have too low an osmolality), they cause fluid to migrate across red cell membranes and can inflate and eventually burst the cells (hemolysis). Therefore, plain water, even if sterile, can never be given to a patient as an IV solution without the risk of causing harm or death.

Providing IV solutions in a crystalline form for reconstitution at the time of use, as described herein, may provide benefits over conventional systems in that the number of IV doses prepared in the pharmacy can be reduced, and the potency, purity and sterility of such doses may be much better assured than with pharmacy-based admixture. Providing automation of such reconstitution using devices and processes as described herein may provide additional benefits over conventional systems in that reconstitution can be performed in approximately real time in such devices on patient care units in hospitals rather than having to be centralized in the pharmacy. Irrespective of location, this automation may significantly reduce the space, facilities and personnel currently required to generate IV doses in comparison with conventional admixture processes. Decentralization of reconstitution to the patient care areas may allow IV doses to be more immediately available for patient use.

According to various embodiments disclosed herein, a system is provided having one or more of each of two primary devices. The first device is an IV solution container designed to be filled with the crystalline contents of an IV solution dose, and reconstituted with sterile water for injection just before use. The containers may be of varying sizes as required by the IV doses' intended final volumes. The containers for the IV doses may be manufactured having only crystalline contents. Such crystalline doses are smaller, lighter, less costly to ship, and less costly to store than conventional liquid IV containers.

Because the drugs are in crystalline form, they have long physical stability, making manufacture under FDA regulations more practical. The need for centralized pharmacy preparation may also be reduced. Each container can be reconstituted with an appropriate amount of an appropriate diluent (e.g., sterile water) to produce a ready-to-administer dose.

Each container may include a sealed cavity formed by a rigid portion and an expandable sealing membrane. The rigid portion and the expandable sealing membrane may be configured to preserve the potency, purity, and sterility of its crystalline contents for, for example, at least two years or longer. The rigid portion and the expandable sealing membrane may be configured to preserve the potency, purity and sterility of its fluid contents, after reconstitution, for at least the period of the chemical stability of its contents.

The rigid portion may be configured to be stackable, so that a large number of containers can be stored in a small space. The rigid portion may include features that make the container machine-manipulable (e.g., by a robotic arm and a gripping device attached to the robotic arm) to facilitate automated selection, reconstitution, labeling and dispensing. The rigid portion may include at least one flat surface shaped to accept a flat label. Unlike round or oblong current containers, labels on the flat surface are flat and easy to read, and contents do not become hidden by folds in the container as it drains.

The second primary device may be a storage and reconstitution device configured to store the containers as described, and reconstitute them on demand with appropriate labeling and documentation. Storage and reconstitution devices having a variety of sizes may be provided. For example, relatively large devices might be used in a centralized preparation area while smaller storage and reconstitution devices might be placed in patient care areas to prepare, label and "vend" completed doses as they are needed by the caregivers for patients in that area.

The storage and reconstitution device(s) can be networked. For example, multiple such devices can be built into a network of delivery systems from which the most commonly used doses in a patient care area are prepared and available in that area while less commonly used preparations are centrally prepared (e.g., in a pharmacy). The network of storage and reconstitution devices may include a control system that delivers (e.g., pushes from the central system) dose requests to the appropriate device based on the known contents of that device across the network and its proximity to the patient who will receive the dose. For example, each device may provide updated content information regarding the containers stored therein and the control system may select a device for reconstitution based on the received content information from the various devices and/or based on known location, patient, or other information related to each device.

Each storage and reconstitution device may contain a large diluent reservoir for reconstitution of the IV doses. In one embodiment, each storage and reconstitution device has storage of at least 100 IV solution containers (e.g., stacked containers) with crystalline contents. Each storage and reconstitution device may have a mechanism for selection of a specific container, containing specific crystalline contents, and for verification that the mechanism (e.g., a robotic arm) selected the correct container.

Each storage and reconstitution device may include a mechanism to determine the correct amount of diluent (e.g., sterile water) to inject into each container for its proper dose reconstitution and to deliver that required volume of diluent. Each storage and reconstitution device may include a mechanism (e.g., another robotic arm or other motorized agitator) to agitate the container after reconstitution to ensure complete dissolution of contents. Each storage and reconstitution device may include a mechanism by which to verify that the correct amount of diluent was delivered to the container (e.g., by monitoring the amount of diluent pumped and/or monitoring the weight of the container or a visual indicator of the amount of fluid in the container).

Each storage and reconstitution device may include a mechanism (e.g., a camera, a window for an operator, or a spectral or chemical analyzer as would be understood by one skilled in the art) by which to verify that the contents are completely dissolved, following reconstitution. Each storage and reconstitution device may include a mechanism by which to print and apply a patient-specific label to the completed dose (e.g., to the rigid portion of the housing of the container.

Each storage and reconstitution device may include communications circuitry and processing circuitry configured to (a) receive doses that require preparation (e.g., from a centralized server that pushes dose orders to the device via a network), (b) verify that the device has the correct container required by each received dose, (c) maintain a queue of doses to be prepared and a priority of the items in that queue (e.g., based on patient need), (d) prepare doses in order by the priority, (e) select the next most appropriate dose to prepare from the queue and record the date/time of selection, (f) select the appropriate solution container from the storage of containers in the storage and reconstitution device, (g) verify that the correct container was selected, (h) record the identity, lot, expiration date, and, if desired, serial number of the container, (i) determine the correct amount of diluent required for the container, (j) acquire and deliver the correct amount of diluent to the container to reconstitute the contents therein, (k) verify that the correct amount of diluent was applied into the container, (l) capture and record the date/time at which reconstitution was completed, (m) cause robotic components in the device to agitate the mixture to ensure complete dissolution, (n) verify complete dissolution and record metrics, (o) compute a beyond-use date for the prepared dose based on the physical and chemical characteristics of the mixture, (p) prepare, print and apply a label to the flat surface of the container containing appropriate patient, content, expiration dating, bar codes, and other information as may be required by law or custom, (q) capture an image of the competed label, (r) capture the date and/or time the label was applied as the dose completion date time, (s) capture the date and/or time that the dose was removed from the storage and reconstitution device and the identity of the person (e.g., a caretaker) removing the dose, (t) report some or all the above operations and information to a control process running at a central server on the network, and/or operate other components of the device to perform other operations as described herein.

In one or more embodiments, multiple storage and reconstitution devices may be provided at various locations to form a network of such storage and reconstitution devices. A control system for one or more storage and reconstitution devices may include, for example, a control server with processing circuitry, memory, and communications components configured to (a) receive doses (e.g., from physician devices, healthcare facility systems, pharmacy systems or other suitable devices) to be prepared by the network of devices, (b) assign and update dose priority based on information such as time due, order parameters (e.g., STAT) etc., (c) permit a dose to be assigned to a particular storage and reconstitution device for preparation only when such preparation would result in a dose that is potent, pure and sterile at the time it is to be administered, (d) maintain a preparation record for each dose, the preparation record including one or more of the date and/or time received from a source system, dose details, the date and/or time and device that the dose was queued to a specific storage and reconstitution device, the current status of the dose, the date and/or time preparation of the dose was begun, the date and/or time a container within the storage and reconstitution device was selected, the identity (e.g., the national drug code or NDC), lot, expiration date and serial number of the container selected, the date and/or time the container was reconstituted and the lot and serial number of the diluent container, the date and/or time the container was agitated, the date and/or time and metrics by which the container was determined to be properly filled with diluent, the date and/or time the label was printed and applied, the image of the labeled dose with a partial or complete image of the label, and the date and/or time and by whom the dose was retrieved from the device, (e) provide access, at one or more user interfaces (e.g., at the control system or at a remote location such as a nursing station, a pharmacy, or a healthcare facility), for location, viewing or printing of individual preparation records, (f) provide access, at one or more user interfaces to preparation record data and/or summaries of the preparation record data that present metrics on the IV dose preparation system, and (g) provide users with the ability to forward information to analytics software systems such as the Medication Knowledge Portal available from CareFusion Corporation.

According to various embodiments, the system may include multiple features and technologies that, in conjunction, form a system that provides nearly-ready-to-administer IV doses that have been manufactured under appropriate guidelines (e.g., the cGMP (21 CFR 210-211)) and can be mechanically reconstituted to produce high-quality doses in real time on the patient care unit or in the pharmacy. In various embodiments, IV solutions may be delivered in crystalline form that contain both hydration chemicals (e.g., salts and sugars) and therapeutic drugs. The crystalline contents may be provided in containers that are dimensionally precise enough for mechanical manipulation and that do not require sharp objects such as needles for fluid delivery. In this way, IV solution containers may be provided that can be stacked for shipping and storage and automatically retrieved from storage, manipulated for reconstitution, and labeled when needed for IV delivery of the therapeutic drugs to a patient.

FIG. 1 illustrates a system 100 for storage and reconstitution of IV solutions containing therapeutic drugs, according to an embodiment. As shown in FIG. 1, system 100 may include one or more storage and reconstitution devices 102, one or more IV solution containers 104, and a control system such as control system 108 in which storage and reconstitution devices 102 are communicatively coupled to the control system via network 106.

Network 106 may be, for example, a wired or wireless network. Network 106 may be a local area network (LAN) or a wider area network such as the Internet. Network 106 may include wired and/or wireless connections between various components and systems and may include portions of a wireless LAN, one or more portions of telephone, cellular, satellite, cable, fiber-optic, or other communications network(s).

Storage and reconstitution devices 102 may be provided at various locations. For example, network 106 may be coupled to storage and reconstitution device in a patient care area of a healthcare facility (e.g., at or near a nursing station, in an intensive care unit (ICU) in a neonatal intensive care unit (NICU), in a pharmacy (e.g., a standalone pharmacy or a pharmacy at the healthcare facility), or at a hazardous materials location (e.g., a facility in which the storage and reconstitution device is coupled to or disposed within a hazardous gas exhaust system for safely disposing of hazardous chemicals, gasses, or fumes)). Control system 108 may receive an order (e.g., an order for a dose of an IV medication from a pharmacy or a physician device). Control system 108 may direct the order to one of devices 102 based on (a) the location of the patient relative to the device, (b) the availability of containers 104 having medications for that order in the device, (c) the commonality of that order, (d) the hazardousness of that order, and/or (e) or other data received from devices 102 or other information systems as described herein.

For example, a particular IV medication may be commonly used by patients treated by nurses that use a particular nursing station. A storage and reconstitution device 102 at or near that nursing station may be stocked with IV solution containers having crystalline IV solution and crystalline medication for making that commonly used IV medication. In this way, the commonly used order can be readily filled at the nursing station, thereby reducing the wait time for patients to receive the dose and reducing the cost and weight of transporting the doses to that nursing station. Control system 108 may direct orders for patients of the nurses that use that nursing station to the storage and reconstitution device at that nursing station. Control system 108 may also direct orders for the commonly used dose that is stored in the storage and reconstitution device at or near that nursing station to that storage and reconstitution device (e.g., for patients of nurses at that nursing station or for patients at other locations such as patients of nurses at nursing stations near that nursing station).

As another example, control system 108 may direct orders for chemotherapy drugs or other drugs that may produce hazardous waste or hazardous medications to a storage and reconstitution device at a hazardous materials facility or at a pharmacy capable of handling hazardous medications.

Each storage and reconstitution device 102 may include various storage components and robotic devices for storage and manipulation of IV solution containers 104. IV solution containers 104 may each have physical features that facilitate manipulation and storage by storage and reconstitution device 102. For example, each IV solution container 104 may include a relatively rigid portion of a housing. The rigid portion may include features for stacking the IV solution containers and/or features for locating, grasping, and agitating the containers using robotic components of storage and reconstitution device 102. Further details of storage and reconstitution devices 102 and IV solution containers 104 are provided hereinafter.

Each IV solution container 104 may be provided with crystalline hydration chemicals and a crystalline drug. In this way, IV solutions can delivered in a crystalline form for reconstitution at the time of use, a much smaller number of IV doses may be required to be prepared in the pharmacy, and the potency, purity and sterility of such doses can be better assured than with pharmacy-based admixture.

Storage and reconstitution devices 102 may provide sufficient automation of storage and reconstitution, that such reconstitution may be performed in real time in such devices on patient care units in hospitals (e.g., rather than, or in addition to centralized processes in the pharmacy). This type of automation may significantly reduce the space, facilities and personnel needed relative to those employed to perform admixture of drugs to IV containers using conventional processes. Moreover, decentralized distribution of the locations of storage and reconstitution devices 102 (e.g., to various patient care areas or a hazardous materials facility), instead of or in addition to in a pharmacy may facilitate providing doses more immediately for patient use when needed.

Figure 2:
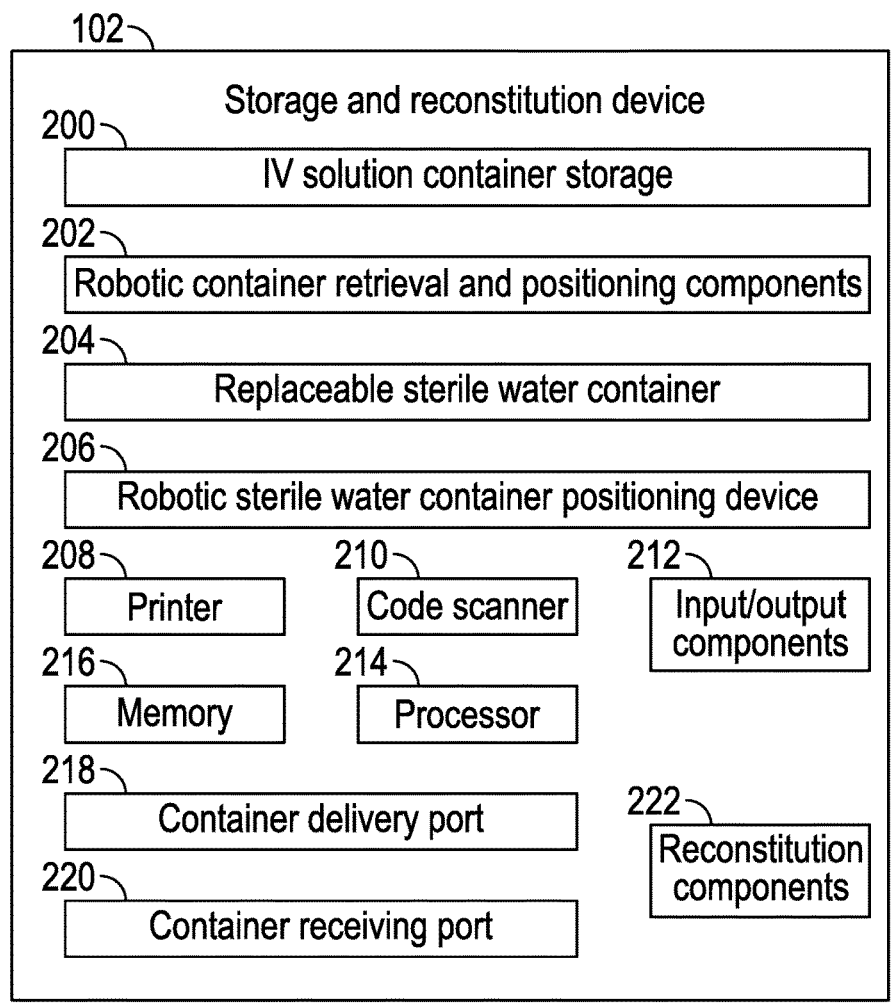
FIG. 2 illustrates a block diagram of an exemplary embodiment of a storage and reconstitution device in accordance with aspects of the present disclosure.

FIG. 2 shows a block diagram of storage and reconstitution device 102 in accordance with an embodiment. As shown, storage and reconstitution device 102 may include components such as IV solution container storage components 200 in addition to robotic container retrieval and positioning components 202. For example, storage components 200 may include a storage housing containing one or more shelves that are accessible by robotic container retrieval and positioning components 202 such as a robot arm having grasping components for lifting and removing an IV solution container 104 from the storage 200. The robot arm may be sized and arranged to be able to locate and select the appropriate container for each dose description.

Storage and reconstitution device 102 may also include one or more fluid containers such as sterile water container 204 (e.g., a replaceable sterile water container) that store sterile water to be provided into the IV solution containers by storage and reconstitution device 102 to reconstitute crystalline hydration chemicals and therapeutic drug within the container. Container 204 may be a metal or plastic tank, a large (e.g., 100 L or 200 L) manufactured bag of sterile water, or other suitable fluid container. Because container 204 may be large and/or heavy, storage and reconstitution device 102 may include components for lifting and proper positioning of one or more sterile water containers such as robotic sterile water container positioning device 206. In other embodiments, storage and reconstitution device 102 may include a mechanical water purification system that could render sterile water for injection out of local tap water.

Sterile water from container 204 may be provided to reconstitution components 222 that direct an appropriate quantity of the sterile water therein into a particular IV solution container 104. Reconstitution components 222 may include robotic positioning and/or agitation devices in addition to optical devices for ensuring reconstitution has been successful, and labeling and scanning devices for ensuring the appropriate container has been selected and providing patient-specific labeling for a completed IV solution container. Additional details of reconstitution components 222 are provided hereinafter.

Storage and reconstitution device 102 may also include computing components such as printer 208 (e.g., a label printer or labeler), code scanner 210 (e.g., an optical, radio-frequency, or other code scanner), input/output components 212 (e.g., a keyboard, a display, a touchscreen, an optical or radio-frequency identification scanner for identifying a caregiver, a mouse, communications circuitry, and/or other input components and/or output components with which a caregiver, another user, or a remote device can interact with storage and reconstitution device 102). The computing components of storage and reconstitution device 102 may also include one or more processors 214 and memory 216 (e.g., volatile or non-volatile memory). Coded instructions may be stored using memory 216 that, when executed by processor 214 cause the computing components, robotic components, and/or other mechanical and/or electronic components of storage and reconstitution device 102 to cooperate to safely store, retrieve, and manipulate sterile water container 204 and one or more IV solution containers 104 to prepare reconstituted solutions within the one or more IV solution containers responsive to receiving an order from control system 108 (see FIG. 1). Printer 208, code scanner 210, memory 216, and processor 214 may cooperate to print and apply a patient-specific label to the IV solution container 104 for each dose. A patient-specific label may include information necessary to meet legal and health-system requirements for providing IV drugs to a patient.

In one suitable example, control system 108 may receive multiple orders for IV drugs for patients in various locations. Control system 108 may determine the locations of the patients, locations of various storage and reconstitution devices 102 relative to the patient locations, and the contents of the IV solution containers stored within each of the storage and reconstitution devices 102. Control system 108 may distribute orders to the various storage and reconstitution devices 102 at particular times determined based on the order information, the patient locations, and the device locations.

For example, an order for a first IV drug for a patient in a first patient care area may be provided by control system 108 to a first storage and reconstitution device 102 located at that first patient care area. The first storage and reconstitution device 102 may store IV solution containers 104 having crystalline forms of various drugs commonly used in that patient care area, each in combination with suitable crystalline hydration chemicals. In another example, control system 108 may determine that the first storage and reconstitution device 102 does not have any of the IV solution containers suitable for reconstitution the first IV drug. In such a scenario, control system 108 may direct the order for the first IV drug to, as examples, (a) a second storage and reconstitution device 102 (e.g., a second device that is located at a pharmacy associated with the first patient care area), or to (b) a third storage and reconstitution device 102

(e.g., a third device that is located in a second patient care area). In one suitable example, control system 108 may direct the order to a second patient care area that is adjacent to the first patient care area. In another suitable example, control system 108 may direct the order to a second patient care area that has the next nearest storage and reconstitution device 102.

In some scenarios, IV drugs may include particularly hazardous chemicals. Control system 108 may direct orders for IV drugs that include hazardous chemicals to a storage and reconstitution device 102 that is located at a central hazardous materials facility with additional facility-level safeguards for hazardous materials processing (e.g., clean rooms, exhaust facilities, secure access, etc.).

Storage and reconstitution device 102 may include one or more ports such as container delivery port 218 and container receiving port 220. Container deliver port 218 may be a secure-access port through which completed (e.g., with reconstituted hydration chemicals and therapeutic drug(s)) IV solution containers are delivered from reconstitution components 222 to a caregiver for delivery to a patient. Memory 216 and processor 214 may operate, for example, a secure door or other security barrier of port 218 to allow an IV solution container to be retrieved from port 218 only by an authorized user such as a caregiver for the patient associated with the IV solution container. The authorized user may be identified, for example, using code scanner 210 or by a password or other identifier entered by the caregiver.

A storage and reconstitution device 102 for IV drugs that include hazardous chemicals may include additional safety features for prevention of contamination of the environment with the hazardous chemicals. For example, a storage and reconstitution device 102 for hazardous IV drugs may include an outlet portal (e.g., a portal coupled to container delivery port 218) connected to a tubing of protective material such as transparent impermeable plastic. A completed dose can be issued into, and sealed within an overwrap of the impermeable, but transparent plastic before or while being provided to container delivery port 218, to limit or eliminate the potential to contaminate the environment with the hazardous material.

Container receiving port 220 may be a relatively larger port at which one or more IV solution containers (e.g., trays having one, two, three, or more stacked layers of IV solution containers) can be input into storage and reconstitution device 102 for storage and later reconstitution. Each of the IV solution containers input into storage and reconstitution device 102 via container receiving port 220 may include crystalline hydration chemicals and crystalline drug(s) to be reconstituted using sterile water from sterile water container 204 by reconstitution components 222.

Figure 3:
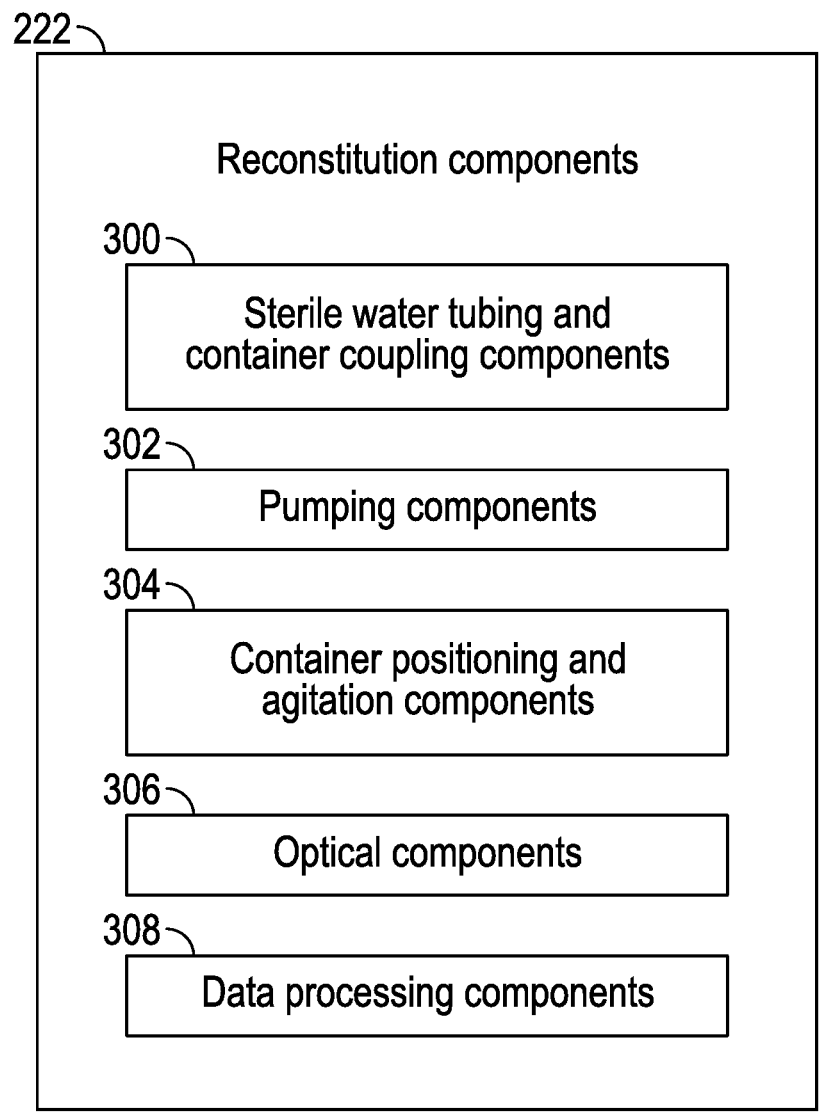
FIG. 3 illustrates a block diagram of an exemplary embodiment of reconstitution components of a storage and reconstitution device in accordance with aspects of the present disclosure.

FIG. 3 shows a block diagram of reconstitution components 222 of storage and reconstitution device 102, according to an embodiment. As shown in FIG. 3, reconstitution components 222 may include sterile water tubing and container coupling components 300, pumping components 302, container positioning and agitation components 304, optical components 306, and data processing components 308.

Sterile water tubing and container coupling components 300 may include tubing that extends from sterile water container 204 to a connector (e.g., a Luer-type connector, a SmartSite® connector, or other suitable connector such as a needle-free connector) configured to couple to a corresponding connector on IV solution container 104 to fluidly couple the source of sterile water to the IV solution container. Pumping components may be disposed at the sterile water container, at the connector, or anywhere along the tubing of sterile water tubing and container coupling components 300 such that the pumping components can manipulate a portion of the tubing or a pumping interface to pump the sterile water from the sterile water source to the IV solution container.

Container positioning and agitation components 304 may be formed as a part of robotic container retrieval and positioning components 202 (see FIG. 2) or may form a separate container manipulation system from robotic container retrieval and positioning components 202. Container positioning and agitation components 304 may include one or more robotic arms having grasping calipers or other components configured to (a) grasp and release an IV solution container, (b) position the IV solution container for coupling to the connector of sterile water tubing and container coupling components 300, (c) agitate the IV solution container, position the IV solution container for optical and/or user verification of reconstitution (e.g., using optical components 306 such as a camera, a laser/detector device or other optical verification device), and (d) deliver the IV solution container to the container delivery port 218.

In one embodiment, optical components 306 may include a light source (e.g., a laser light source or an light-emitting-diode light source) configured to illuminate the fluid within an IV solution container and a light detector (e.g., an imaging detector or a spectrometer) configured to determine (e.g., in cooperation with data processing components 308), based on light that passes through the solution and/or reflects from the solution, whether reconstitution has been successful. In another embodiment, optical components 306 may include a camera that captures an image of the IV solution container following agitation and provides the image to a user (e.g., using a display of input/output components 212). In another embodiment, optical components 306 may include a window through which a user can directly view the IV solution container within reconstitution components 222 for visual verification of reconstitution.

Data processing components 308 may include one or more processors, memory, and/or other computing equipment for verification of reconstitution. Data processing components 308 may include processor 214 and memory 216 of FIG. 2 or may be additional processing and data storage components.

Figure 4:
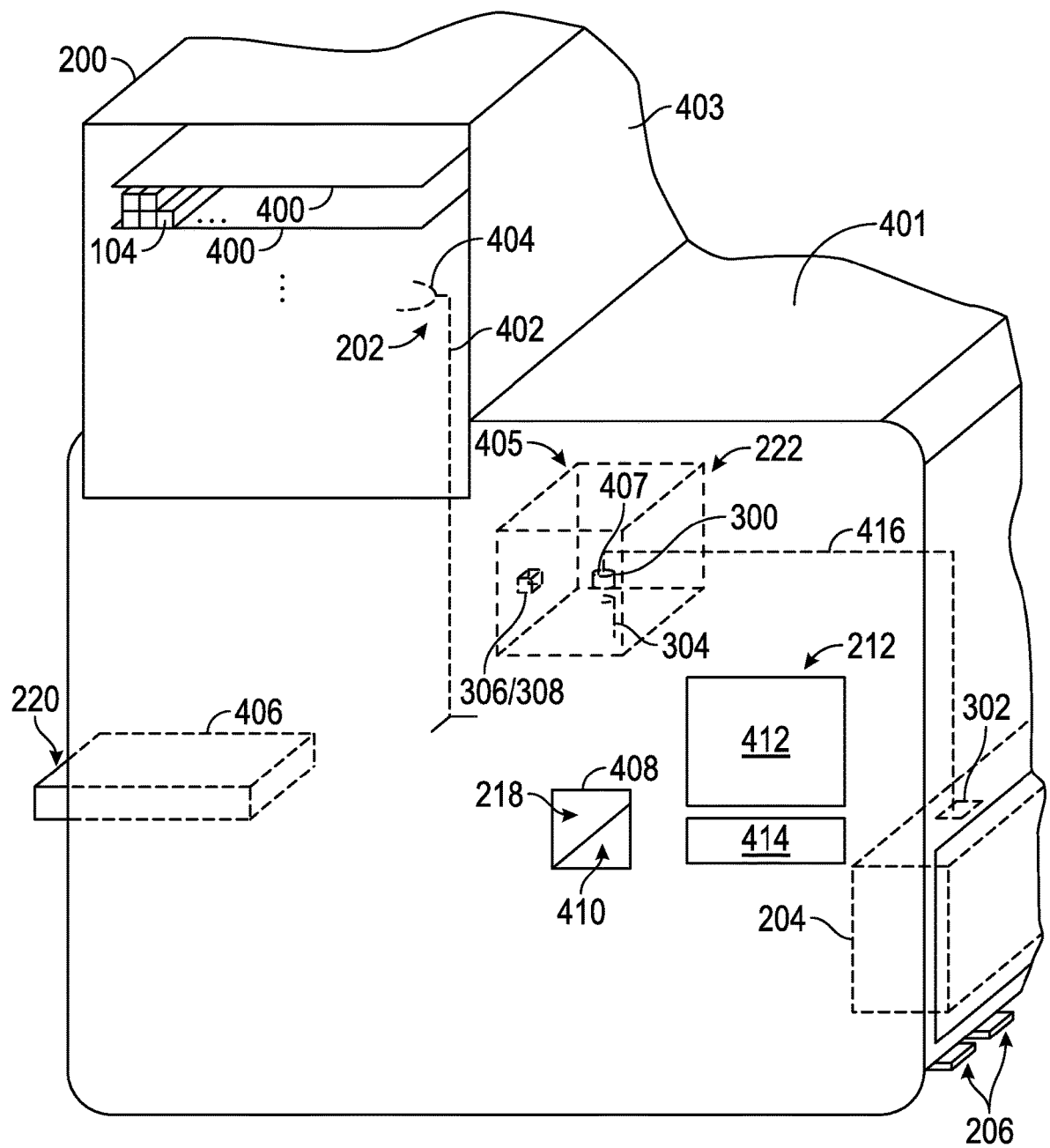
FIG. 4 illustrates a perspective view of an exemplary embodiment of a storage and reconstitution device in accordance with aspects of the present disclosure.

FIG. 4 shows an illustrative diagram of a configuration for storage and reconstitution device 102, according to an embodiment. In the example of FIG. 4, storage and reconstitution device includes operating portion 401 with storage housing 403 extending therefrom. As shown, storage housing 403 encloses IV solution container storage 200 within which stacked IV solution containers 104 are stored on shelves 400.

Robotic container retrieval and positioning components 202 may include robotic arm 402 extending from and/or movable from operating portion 401 into storage housing 403. Robotic arm 402 may include grasping portion 404 at a distal end thereof. Grasping portion 404 may be formed from, for example, a pair of actuatable calipers having features that correspond to engagement features on a housing of each of IV solution containers 104.

IV solution containers 104 may be stacked on shelves 400 at locations known to computing equipment so that robotic arm 402 can be moved to retrieve a particular IV solution container 104 having crystalline contents corresponding to a particular order, and to move the retrieved container 104 to reconstitution components 222.

In the example of FIG. 4, storage housing 403 extends from the top of operating portion 401. In this way, storage for containers 104 may be disposed in an unused portion of a patient care ward such as in the overhead ceiling space of the patient care ward. However, this is merely illustrative. In other embodiments, storage housing 403 may extend from a sidewall, a rear wall, or a bottom wall of operating portion 401. In other embodiments, shelves 400 may be disposed within operating portion 401.

In the example of FIG. 4, input-output components 212 are implemented with display 412 (e.g., a touchscreen or non-touch display) and keyboard 414 disposed in outer wall of operating portion 401. Container delivery port 218 may include secure door 408 and, in some embodiments, conveyor belt 410 that delivers a completed IV solution container to port 218. However, this is merely illustrative. In some embodiments, port 218 may have an unsecured door, may be provided without a door, and/or with or without a conveyor belt. For example, in one embodiment, robotic arm 402 (or an additional robotic arm) may be provided with the capability of moving a completed IV solution container from reconstitution components 222 to port 218.

As shown in FIG. 4, reconstitution components 222 may include chamber 405 within which container positioning and agitation components 304 (e.g., a robotic arm in the chamber in the implementation of FIG. 4), optical and data processing components 306/308 (e.g., a camera disposed within the chamber and configured to capture images of an IV solution container within the chamber), and sterile water tubing and container coupling components 300 are disposed for reconstitution operations.

Sterile water tubing and container coupling components 300 may include tubing interior to the chamber and connector 407 (e.g., a Luer connector, a SmartSite® connector, a Texium® connector, or other needle-free or needle based connector) for fluidly coupling to an IV solution container 104. Tubing coupled to connector 407 may be fluidly coupled, via tubing 416 to a source of sterile water such as a filtration system or sterile water container 204 as in the implementation of FIG. 4. In the example of FIG. 4, pumping components 302 are disposed at the sterile water container and arranged to pump the sterile water from the sterile water container, through tubing 416 to connector 407 when an IV solution container having crystalline hydration chemicals and/or crystalline drug(s) is coupled to connector 407.

In use, system 102 may be operated to reconstitute various different IV solutions and/or medication doses by adding sterile water, via connector 407, to various containers 104. Connector 407 may include one or more components that prevent cross-contamination between containers 104. For example, connector 104 may include one or more components such as valves (e.g., check valves) that prevent a solution being reconstituted from flowing backwards (e.g., in a retrograde flow) into the diluent supply line 416 to prevent contamination of line 416 with the contents of the solution being reconstituted. In some embodiments, connector 407 may include a replaceable and/or disposable connector interface for coupling to container 104. In this way, a particular connector interface of connector 407 may be used only for reconstitution of a particular IV solution and replaced when system 102 is operated to reconstitute a different solution and/or after a predetermined number of reconstitution operations. A connector interface of connector 407 may be replaceable automatically, and without user intervention, by system 102 during operation (e.g., using a robotic arm of the system to remove and dispose of one connector 407 and to obtain and install a new connector 407).

Robotic sterile water container positioning device 206 is shown in FIG. 4 implemented as extendible platforms arranged to extend from beneath operating portion 401 to lift container 204 into position within operating portion 401. Container input port 220, in the example of FIG. 4, includes conveyor belt 406 configured to move a tray of multiple stacked IV solution containers, each having crystalline hydration chemicals and crystalline drug(s), from the input port into operating portion 401, to be moved to shelves 400 by robotic container retrieval and positioning components 202. Each tray of stacked IV solution containers 104 (and/or each container 104) may be labeled (e.g., using a bar code or a radio-frequency identification (RFID) code) with a label that is scanned upon input. Robotic container retrieval and positioning components 202 may place each input tray at a position on shelves 400 that corresponds to a storage area for a particular type of IV solution container.

Figure 5:
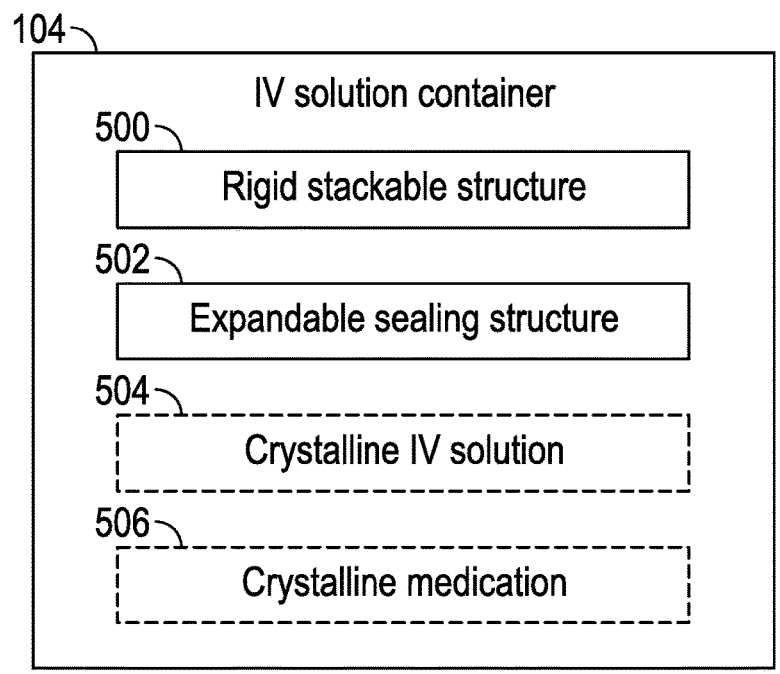
FIG. 5 illustrates a block diagram of an exemplary embodiment of an IV solution container in accordance with aspects of the present disclosure.

FIG. 5 shows a block diagram of an IV solution container 104 according to an embodiment. As shown in FIG. 5, IV solution container 104 may include stackable structure 500 that is relatively more rigid than expandable sealing structure 502. Rigid stackable structure 500 may form a rigid, stackable machine-manipulable portion of a housing of the IV solution container 104. Expandable sealing structure 502 may be sealingly attached to rigid stackable structure 500 to form a remaining portion of the housing of IV solution container 104. Attaching expandable sealing structure 502 to structure 500 may form a cavity in the housing within which a crystalline IV solution 504 (e.g., crystalline hydration chemicals as described herein such as crystalline Sodium Chloride or crystalline Dextrose in various quantities and/or concentrations) and/or a crystalline medication (e.g., a crystalline therapeutic drug as described herein) may be enclosed.

Rigid stackable structure 500 may, for example, be a molded plastic or metal structure having features and a rigidity suitable for stacking and machine manipulation (e.g., by robotic components) in 3-dimensional space. Sealing structure 502 may be formed from an oversized or stretchable membrane sealed to rigid structure 500 to form a cavity therebetween. The cavity may be configured to maintain the potency, purity and sterility of the crystalline contents during manufacture, delivery through the supply chain, and storage in a healthcare facility (e.g., for a period of up to or more than two years). The cavity may be configured to maintain the potency, purity and sterility of the reconstituted solution for at least the period of physical/chemical stability of the ingredients (e.g., for a period of up to 24 hours, between 24 hours and 36 hours, up to 36 hours, or more than 36 hours). For example, sealing structure 502 may be an oversized plastic sheet that is larger in surface area than the area bounded by the perimeter of structure 500 at which sealing structure is attached to structure 500 so that the excess material of the sheet can accommodate fluid added to the cavity. In another example, sealing structure 502 may be formed from a sheet of stretchable material that, when the container is unfilled with fluid, forms a substantially planar seal over and that, when fluid is added to the container, stretches to increase the volume of the cavity responsive to fluid pressure therein.

Each container 104 may be provided with a label that permits automatic (e.g., robotic) location and use of a specific container with appropriate crystalline contents and recording of the information required for traceability by, for example, the Drug Supply Chain Security Act. Each container 104 may have one or more ports that allow water to be delivered to the container without requiring a needle.

Figure 6:
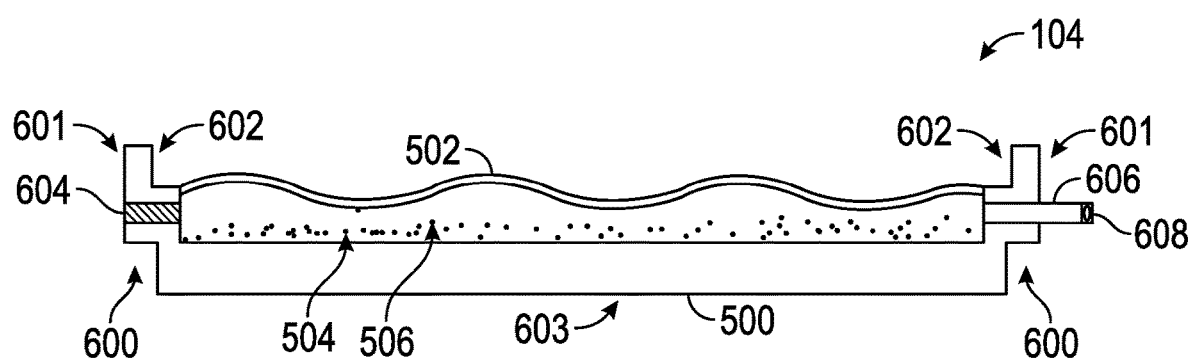
FIG. 6 illustrates a cross-sectional view of an exemplary embodiment of an IV solution container prior to reconstitution in accordance with aspects of the present disclosure.

A cross-sectional side view of one exemplary implementation of IV solution container 104 is shown in FIG. 6. As shown in FIG. 6, crystalline IV solution 504 and crystalline medication 506 may be sealingly disposed between rigid portion 500 and expandable sealing membrane 502. Rigid portion 500 may include a base portion 603 and sidewall portions 601 that extend substantially perpendicular to base portion 603. In the example shown in FIG. 6, sidewall portions 601 include features such as internal features 602 and external features 600 that facilitate stacking of multiple layers of IV solution containers 104. For example, external features 600 may include a cutout having a shape that corresponds to the shape of a corresponding internal feature cutout 602. In this way, if another IV solution container 104 is placed onto the IV solution container 104 as shown, the external cutout 600 of the additional IV solution container 104 may engage with internal cutout 602 of IV solution container 104 as shown so that the two IV solution containers 104 can be securely stacked. Similarly, if another IV solution container 104 is placed below IV solution container 104 as shown, internal cutout 602 of the additional IV solution container 104 may engage with external cutout 600 of IV solution container 104 as shown so that the two IV solution containers 104 can be securely stacked. In this way, multiple layer stacks of IV solution containers 104 can be formed for storage and shipping.

External features 600 and/or other external or internal features may also correspond in shape to caliper or other gripping features of robotic arms 402 and/or 304 to facilitate secure gripping and machine manipulation of rigid portion 500 of IV solution container 104 for moving, positioning, and/or agitating IV solution container 104. However, features 600 and 602 of FIG. 6 are merely illustrative and other arrangements for the stacking and machine-manipulation features of rigid portion 500 may be provided.

As shown in FIG. 6, rigid portion 500 may include one or more ports such as ports 604 and 606 that extend through rigid portion 500 to allow sterile water to be provided into IV solution container 104 and/or to allow a reconstituted IV drug to be delivered from IV solution container 104 to a patient. In the example of FIG. 6, IV solution container 104 is provided with port 604, formed from an opening and a sealing member in the opening, the sealing member being resiliently penetrable by a needle. For example, to provide sterile water into from IV solution container 104, a needle may be extended through the sealing member of port 604, the needle being fluidly coupled to the source of sterile water. In the example of FIG. 6, IV solution container 104 is provided with port 606, formed from an extension such as a Luer extension having a sealing member 608 disposed therein to form a needle-free port. Port 606 may, for example, be coupled to a corresponding connector (e.g., a corresponding Luer connector, other needle-free connector, or needle-based connector) coupled to tubing of an IV set for providing a reconstituted fluid in from IV solution container 104 to a patient.

For example, for reconstitution, container 104 may be moved, by a robotic arm, toward a corresponding connector within device 102 to couple connector 604 or 606 to the corresponding connector to receive sterile water into the container via the corresponding connector. In another example, for reconstitution, container 104 may be moved to within reach of an extendible or otherwise moveable corresponding connector that is, itself, moved toward container 104 to couple port 604 or 606 to the corresponding container to provide the sterile water to the container. In other examples, various combinations of these operations may be performed to fluidly couple a sterile water source to a container for reconstitution. However, the example of FIG. 6 in which IV solution container 104 includes a needle port and a Luer access port on opposing sides of rigid portion 500 is merely illustrative. In various other embodiments, various combinations of ports may be provided on different sides or on a common side of rigid portion 500 that allow sterile water to be provided into IV solution container 104 and to allow reconstituted solution to be provided from IV solution container 104 to a patient as discussed in further detail hereinafter.

Figure 7:
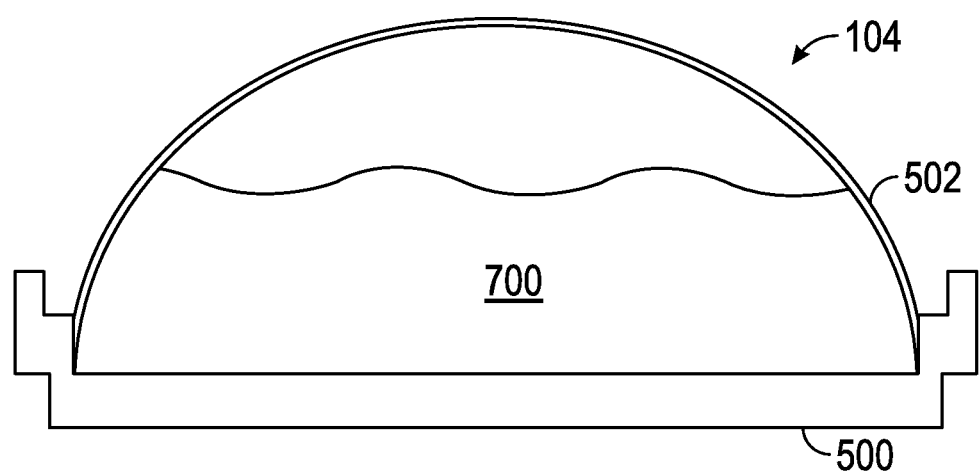
FIG. 7 illustrates a cross-sectional view of an exemplary embodiment of an IV solution container following reconstitution in accordance with aspects of the present disclosure.

FIG. 7 shows another cross-sectional side view of IV solution container 104 following reconstitution operations. As shown in FIG. 7, crystalline IV solution 504 and crystalline medication 506 have been dissolved in sterile water to form medical solution 700 to be provided to a patient intravenously. As shown, expandable sealing member 502 has been expanded (e.g., stretched or merely inflated) due to the addition of the sterile water into IV solution container 104.

Figure 8:
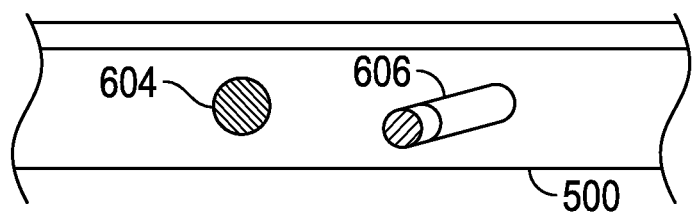
FIG. 8 illustrates a perspective view of an exemplary implementation of fluid ports for an IV solution container in accordance with aspects of the present disclosure.
Figure 9:
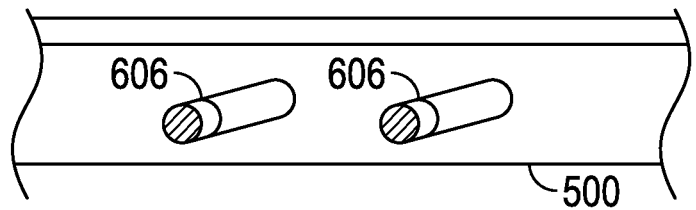
FIG. 9 illustrates a perspective view of another exemplary implementation of fluid ports for an IV solution container in accordance with aspects of the present disclosure.

FIGS. 8 and 9 show alternative embodiments for the fluid ports of IV solution container 104. In the example of FIG. 8, rigid portion 500 includes needle port 604 and extension port 606 (e.g., a Luer access port, a SmartSite® port, a Texium® port, or other needle-free port) on a common sidewall. In the example of FIG. 9, rigid portion 500 is provided with two needle-free ports 606 (e.g., one for delivery of sterile water into the container and one for coupling to an IV set for delivery to a patient) on a common side of rigid portion 500.

Figure 10:
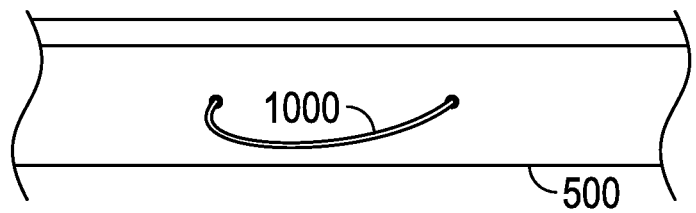
FIG. 10 illustrates a perspective view of an exemplary implementation of a hanging device for an IV solution container in accordance with aspects of the present disclosure.
Figure 11:
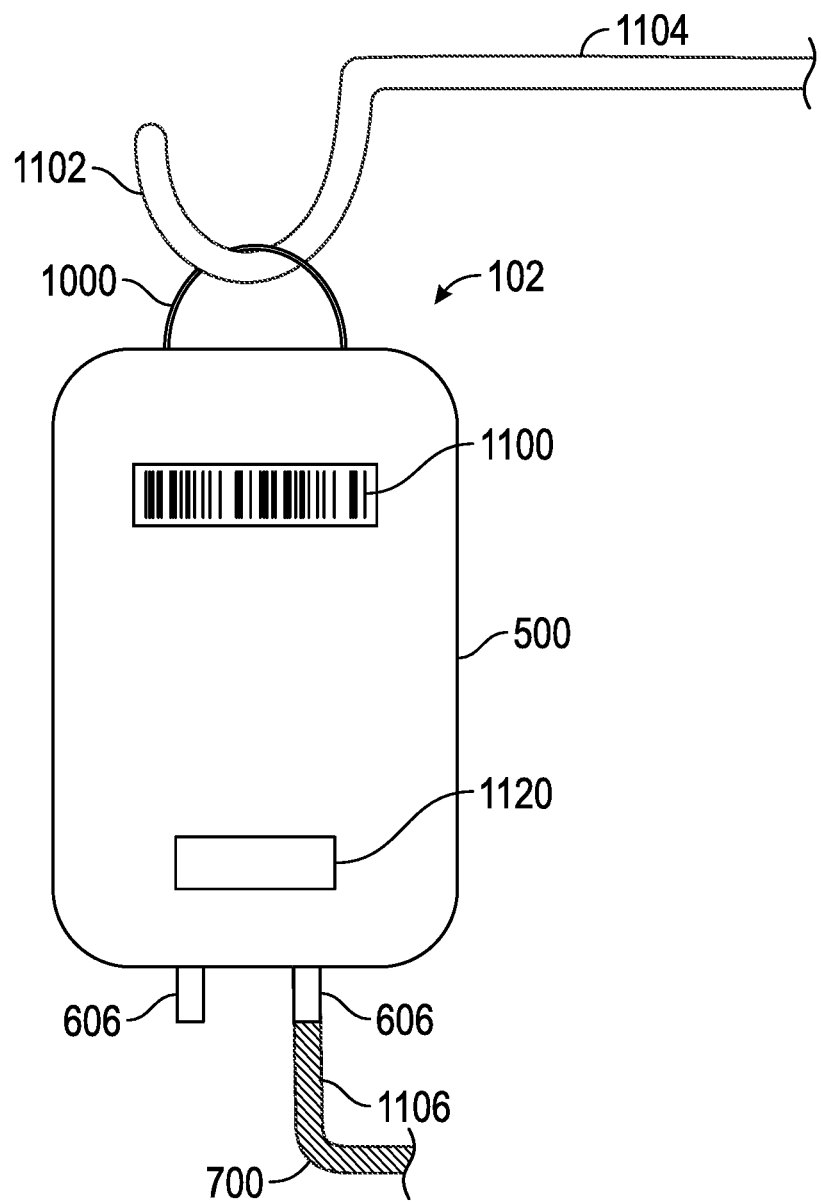
FIG. 11 illustrates an exemplary embodiment of an IV solution container configured for delivery of an IV solution to a patient in accordance with aspects of the present disclosure.

FIG. 10 shows a portion of rigid portion 500 having hanging mechanism 1000 with which IV solution container 104 can be hung on a conventional IV delivery system for delivery of fluids therein to a patient. For example, as shown in FIG. 11, hanging mechanism 1000 is shown hung on hook 1102 of common IV bag holder 1104 (e.g., an IV stand or other IV bag holder) such that port 606 is disposed at the bottom of the container. In this way, tubing 1106 of an IV set can be coupled to bottom port 606 so that medical fluid 700 can be delivered therefrom (e.g., pumped therefrom or delivered by gravity) to a patient.

FIG. 11 also shows a patient-specific label 1100 disposed on rigid portion 500 with information (e.g., information written in text and/or coded information such as bar code information or RFID information) identifying fluid 700, the patient for which the fluid has been prepared, and other information as discussed herein. Label 1100 may be printed and applied to (or printed directly on) rigid portion 500 by, for example, printer 208 of storage and reconstitution device 102. As shown in FIG. 11, rigid portion 500 may include an additional label 1120 (e.g., a label provided thereon during manufacturing and including information related to the original crystalline contents therein and any other shipping, storage, manufacturing, or tracking information generated prior to reconstitution). For example, label 1120 may be used by a storage and reconstitution device to locate, position for storage, and/or track container 102 while within the storage and reconstitution device. Although labels 1100 and 1102 are shown on a back or base portion of rigid portion 500, labels 1100 and 1120 may be placed in other locations such as flat sidewall surfaces of the rigid portion.

Figure 12:
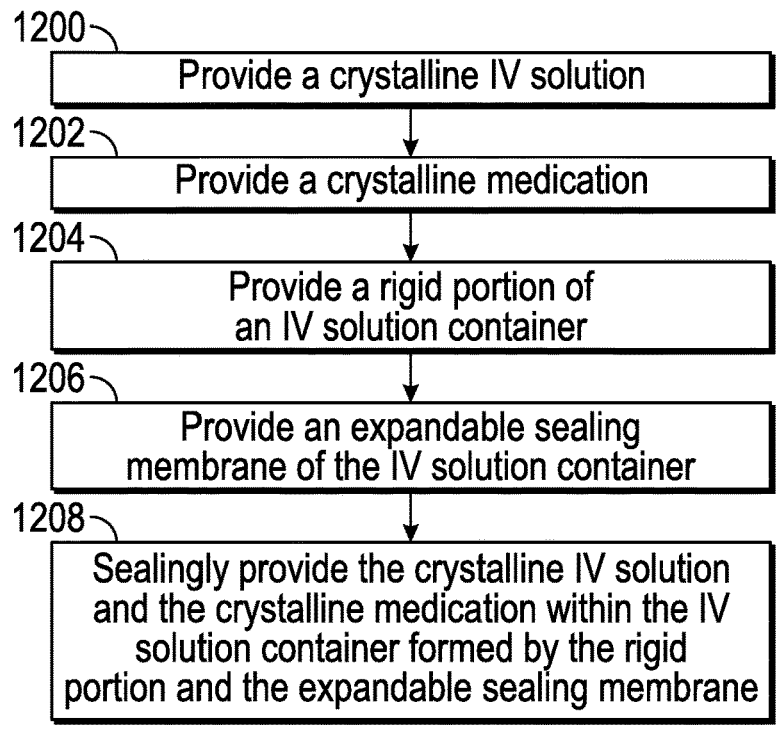
FIG. 12 illustrates a flow chart of exemplary operations that may be performed for manufacturing a stackable IV solution container in accordance with aspects of the present disclosure.

A method of manufacturing an IV solution container 104 for later shipping, storage, reconstitution, and patient delivery is shown in FIG. 12, according to an embodiment.

At block 1200, a crystalline IV solution may be provided. The crystalline IV solution may include crystalline hydration chemicals such as salts and/or sugars. For example, the crystalline IV solution may be sterile crystalline substances containing sufficient salt or sugar content such that, when sterile water is added and the crystalline substances are dissolved in the sterile water, the osmolality of the resulting solution is approximate to that of normal human serum. The resulting solution may be, as examples, 0.9% Sodium Chloride (sometimes referred to as saline, or normal saline solution), Dextrose 5% in Water, or Dextrose 5% in 0.45% Sodium Chloride.

At block 1202, a crystalline medication may be provided. The crystalline medication may include antibiotics, electrolytes, vitamins and minerals, chemotherapy drugs, cardiovascular drugs used to maintain heart rate, control cardiac arrhythmias, or maintain blood pressure at a safe level, heparin, insulin, or other therapeutic drugs that can be reconstituted when sterile water is added to the mixture of crystalline IV solution and crystalline medication.

At block 1204, a rigid portion of an IV solution container may be provided.

At block 1206, an expandable sealing membrane of the IV solution container may be provided.

At block 1208, the crystalline IV solution and the crystalline medication may be sealingly provided within the IV solution container formed by the rigid portion and the expandable sealing membrane. In one embodiment, sealingly providing the crystalline IV solution and the crystalline medication within the IV solution container may include providing both the crystalline IV solution and the crystalline medication into the rigid portion and sealing the crystalline IV solution and the crystalline medication into the IV solution container by attaching the sealing portion to the rigid portion to form a cavity therebetween containing the crystalline IV solution and the crystalline medication. In another embodiment, sealingly providing the crystalline IV solution and the crystalline medication within the IV solution container may include sealingly attaching the sealing portion to the rigid portion and injecting the crystalline IV solution and the crystalline medication between the sealing portion and the rigid portion.

Figure 13:
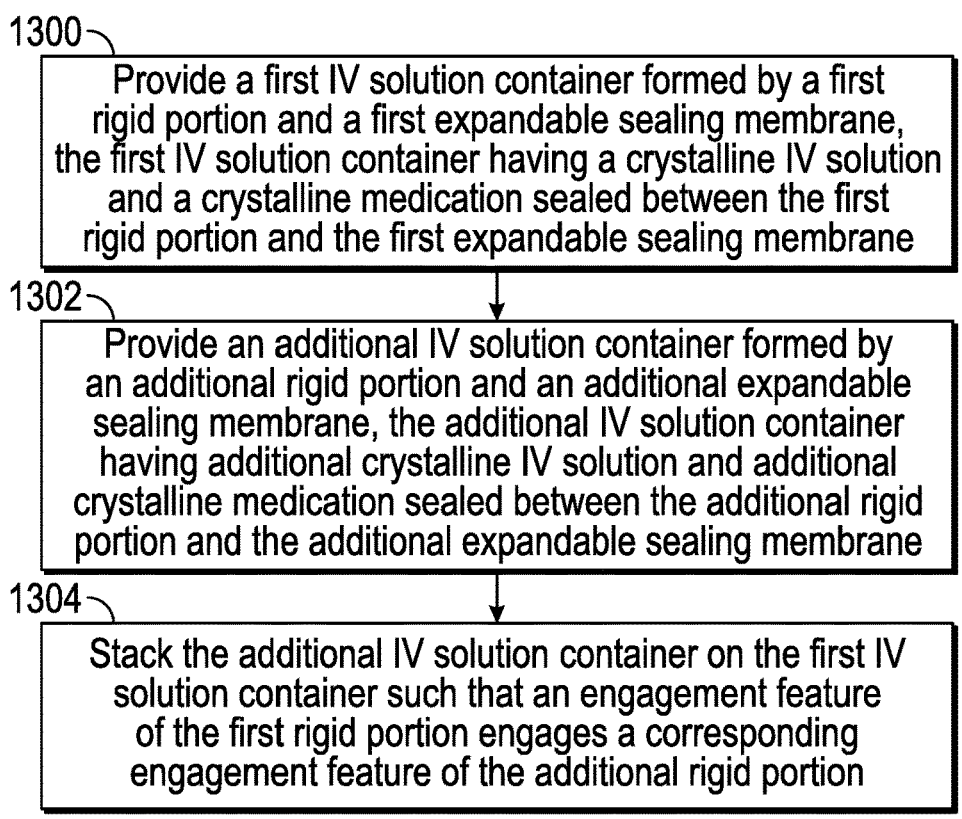
FIG. 13 illustrates a flow chart of exemplary operations that may be performed for preparing a plurality of stackable IV solution containers for shipping in accordance with aspects of the present disclosure.

A method of preparing IV solution containers 104 for shipping and storage is shown in FIG. 13, according to an embodiment.

At block 1300, a first IV solution container formed by a first rigid portion and a first expandable sealing membrane may be provided. The first IV solution container may include a crystalline IV solution and a crystalline medication sealed between the first rigid portion and the first expandable sealing membrane.

At block 1302, an additional IV solution container formed by an additional rigid portion and an additional expandable sealing membrane may be provided. The additional IV solution container may include additional crystalline IV solution and additional crystalline medication sealed between the additional rigid portion and the additional expandable sealing membrane.

At block 1304, the additional IV solution container may be stacked on the first IV solution container such that an engagement feature of the first rigid portion engages a corresponding engagement feature of the additional rigid portion. The IV solution container and the additional IV solution container may each include a label on the rigid portion (e.g., printed on, affixed to, or embedded within the rigid portion) that identifies the crystalline IV solution and the crystalline medication therein. In some implementations, the rigid portion (e.g., the engagement features or the overall size, depth, width, length, volume, or other features of the rigid portion) may be the same for IV solution containers containing different IV solutions and/or different medications so that all IV solution containers can be stacked for shipping and storage. In other implementations, the rigid portion (e.g., the engagement features or the overall size, depth, width, length, volume, or other features of the rigid portion) may have features specific to the IV solution or medication therein so that each stack only includes IV solution containers with common contents. Labels may be human readable and/or machine readable. Machine-readable labels may facilitate automatic location, tracking, storage, and retrieval of the IV solution containers.

The operations described above in connection with blocks 1300, 1302, and 1304 may be repeated until a desired number of stackable IV solution containers, each having crystalline hydration and drug contents have been stacked for shipping and storage.

Figure 14:
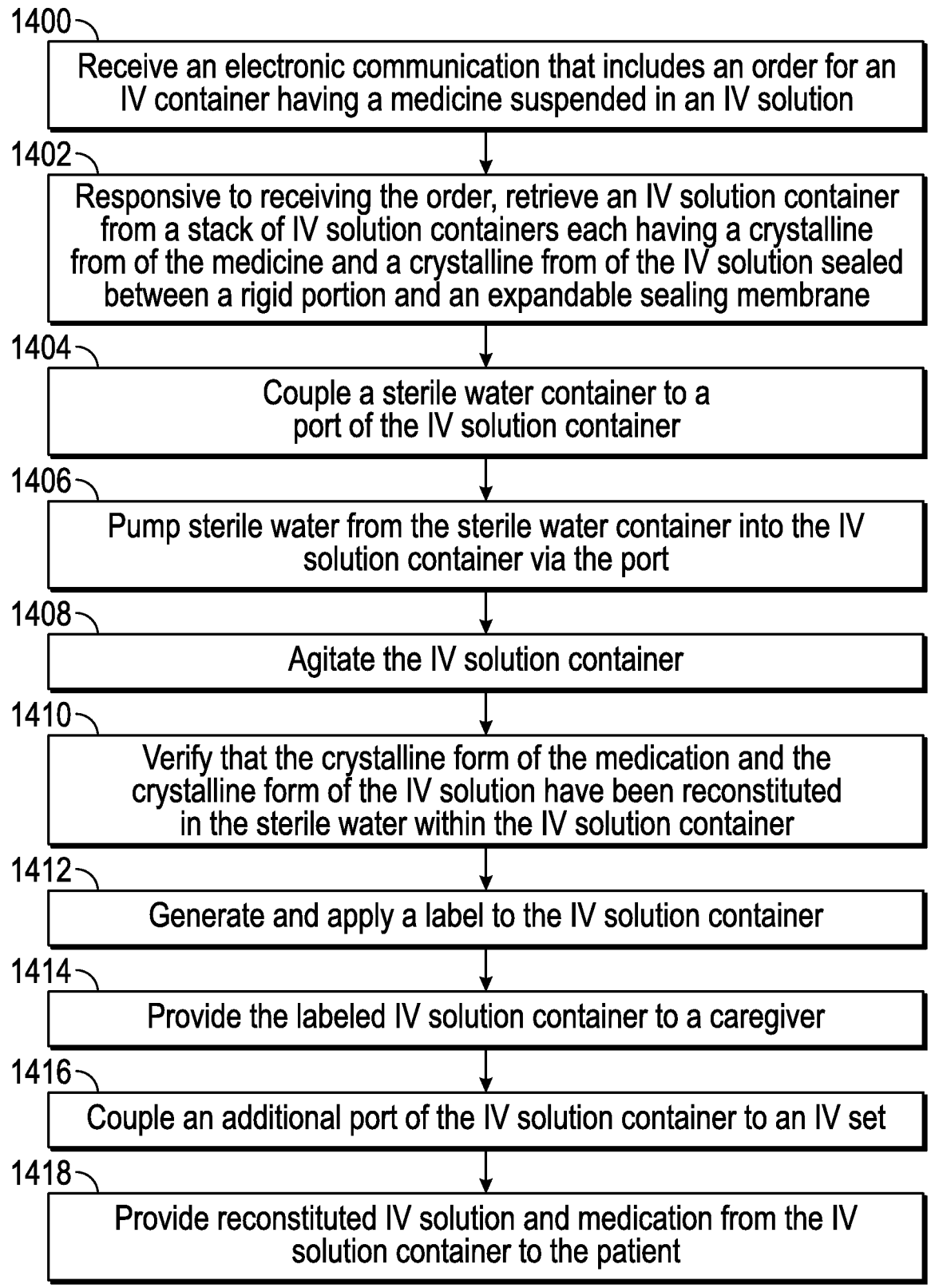
FIG. 14 illustrates a flow chart of exemplary operations that may be performed for reconstituting a medication and an IV solution within a stackable IV solution container in accordance with aspects of the present disclosure.

A method of reconstituting a medical fluid in an IV solution container 104 is shown in FIG. 14, according to an embodiment.

At block 1400, an electronic communication may be received that includes an order for an IV container having a medication suspended in an IV solution to form an IV medication for delivery to a particular patient. The electronic communication may be received from a physician device, from a nursing station, from a pharmacy, from a hospital information system, or from a central reconstitution control system (e.g., control system 108 of FIG. 1) and may be received by communications circuitry of a storage and reconstitution device (e.g., storage and reconstitution device 102 as described herein). The storage and reconstitution device may be located at a nursing station, in a particular area of a healthcare facility (e.g., an ICU, and nICU, an emergency room, or an operating room of a hospital), may be located at a pharmacy, or may be located within a hazardous materials facility (at or remote from the healthcare facility).

At block 1402, responsive to receiving the order, the storage and reconstitution device may retrieve an IV solution container (e.g., an IV solution container 104) from a stack of IV solution containers each having a crystalline form of the medication and a crystalline form of the IV solution sealed between a rigid portion and an expandable sealing membrane of the IV solution container.

At block 1404, a sterile water container (e.g., sterile water container 204 as described herein) may be coupled to a port (e.g., a port 604 or 606) of the IV solution container. Coupling the port of the IV solution container to the sterile water container may include piercing or displacing a sealing membrane of the port with a connector of a fluid line to the sterile water container using robotic positioning components of the storage and reconstitution device.

At block 1406, sterile water may be pumped (e.g., by the storage and reconstitution device) from the sterile water container into the IV solution container via the port. Pumping the sterile water may include pumping a volume of the sterile water sufficient to dissolve the crystalline IV solution and crystalline medication to form the ordered IV medication.

At block 1408, the IV solution container with the sterile water may be agitated (e.g., using container positioning and agitation components 304 as described herein).

At block 1410, the storage and reconstitution device may verify that the crystalline form of the medication and the crystalline form of the IV solution have been dissolved in the sterile water within the IV solution container. Verification operations may include capturing an one or more images of the IV solution container, providing the images to an operator, performing a chemical, spectral, or other test of the solution in the container, or providing a direct view of the container to an operator (as examples).

At block 1412, the storage and reconstitution device may generate and apply a label to the IV solution container. Generating and applying the label may include printing a label and affixing the label to the rigid portion of the container or may include directly printing a label onto the rigid portion. The label may identify (e.g., in human readable and/or machine-readable form) the patient associated with the dose therein, the contents therein, the reconstitution time and date, caretaker identification, physician identification or other suitable information as discussed herein.

At block 1414, the storage and reconstitution device may provide the labeled IV solution container to a caregiver (e.g., via container delivery port 218).

At block 1416, an additional port of the IV solution container may be coupled (e.g., by the caregiver) to an IV set for delivery to the patient identified by the label.

At block 1418, the reconstituted IV solution and medication may be provided from the IV solution container to the patient (e.g., by coupling an IV set to the IV solution container and coupling the IV set to the patient).

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A container including: a housing, having: a stackable, machine-manipulable rigid portion; and an expandable membrane sealingly attached to the stackable, machine-manipulable rigid portion to form an internal volume within the housing the internal volume configured to store at least one crystalline hydration chemical and at least one crystalline therapeutic drug; a first port in the housing, the first port configured to receive sterile water for reconstitution of the at least one crystalline hydration chemical and the at least one crystalline therapeutic drug; and a second port in the housing, the second port configured to receive an intravenous set connector for delivery of a medical fluid formed from the at least one crystalline hydration chemical, the at least one crystalline therapeutic drug, and the sterile water.

Concept 2. The container of Concept 1 or any other Concept, further including the at least one crystalline hydration chemical and the at least one crystalline therapeutic drug stored within the internal volume.

Concept 3. The container of Concept 1 or any other Concept, in which the container comprises a first stackable, machine-manipulable container having the stackable, machine-manipulable rigid portion, and in which the stackable, machine-manipulable rigid portion includes at least one feature configured to engage with a corresponding feature of a second stackable, machine-manipulable container for stacking of the first stackable, machine-manipulable container and the second stackable, machine-manipulable container.

Concept 4. The container of Concept 3 or any other Concept, in which the at least one feature of the stackable, machine-manipulable rigid portion is formed at or near a top surface of the stackable, machine-manipulable rigid portion and in which the stackable, machine-manipulable rigid portion includes at least one additional feature disposed at or near an opposing bottom surface of the stackable, machine-manipulable rigid portion, the additional feature configured to engage with a corresponding feature of a third stackable, machine-manipulable container for stacking of the first stackable, machine-manipulable container, the second stackable, machine-manipulable container, and the third stackable, machine-manipulable container.

Concept 5. The container of Concept 1 or any other Concept, in which the expandable membrane is an oversized plastic membrane.

Concept 6. The container of Concept 1 or any other Concept, in which the expandable membrane is formed from a stretchable sheet of material.

Concept 7. The container of Concept 1 or any other Concept, in which the expandable membrane is configured to expand to accommodate the sterile water.

Concept 8. A storage and reconstitution device, including: a storage region configured to store a plurality of stacked, machine-manipulable containers, each container including at least one crystalline hydration chemical; a sterile water reservoir; and robotic components configured to: move at least one of the plurality of stacked, machine-manipulable containers from the storage region to a connector fluidly coupled to the sterile water reservoir, add sterile water from the sterile water reservoir to the at least one of the plurality of stacked, machine-manipulable containers, agitate the at least one of the plurality of stacked, machine-manipulable containers, verify reconstitution of the at least one crystalline hydration chemical within the at least one of the plurality of stacked, machine-manipulable containers, label the at least one of the plurality of stacked, machine-manipulable containers, and store tracking information for the at least one of the plurality of stacked, machine-manipulable containers.

Concept 9. The storage and reconstitution device of Concept 8 or any other Concept, in which each of the plurality of stacked, machine-manipulable containers includes a housing having a rigid portion and an expandable sealing membrane attached to the rigid portion to form a storage cavity therebetween for the least one crystalline hydration chemical and, in which one or more of the plurality of stacked, machine-manipulable containers includes at least one crystalline therapeutic drug in the storage cavity thereof.

Concept 10. The storage and reconstitution device of Concept 9 or any other Concept, in which the rigid portion of the housing of each of the plurality of stacked, machine-manipulable containers includes at least one feature engaged with a corresponding feature of an additional one of the plurality of stacked, machine-manipulable containers.

Concept 11. The storage and reconstitution device of Concept 8 or any other Concept, in which the robotic components include a robotic arm configured to move the at least one of the plurality of stacked, machine-manipulable containers from the storage region to a connector fluidly coupled to the sterile water reservoir.

Concept 12. The storage and reconstitution device of Concept 11 or any other Concept, further including at least one pump configured to pump the sterile water from the sterile water reservoir to the at least one of the plurality of stacked, machine-manipulable containers.

Concept 13. The storage and reconstitution device of Concept 12 or any other Concept, further including an additional robotic arm configured to agitate the at least one of the plurality of stacked, machine-manipulable containers.

Concept 14. The storage and reconstitution device of Concept 13 or any other Concept, further including a labeler configured to generate the label on a rigid portion of the at least one of the plurality of stacked, machine-manipulable containers.

Concept 15. A system, including: a first storage and reconstitution device at a first location; a second storage and reconstitution device at a second location, in which each of the first and second storage and reconstitution devices includes: a storage region configured to store a plurality of stacked, machine-manipulable containers, each container including at least one crystalline hydration chemical and at least one crystalline therapeutic drug; a sterile water reservoir; and robotic components configured to: move at least one of the plurality of stacked, machine-manipulable containers from the storage region to a connector fluidly coupled to the sterile water reservoir, add sterile water from the sterile water reservoir to the at least one of the plurality of stacked, machine-manipulable containers, agitate the at least one of the plurality of stacked, machine-manipulable containers, and verify reconstitution of the at least one crystalline hydration chemical and at least one crystalline therapeutic drug within the at least one of the plurality of stacked, machine-manipulable containers; and a control system communicatively coupled via a network to the first and second storage and reconstitution devices and configured to push dose orders from clinicians to the first or second storage and reconstitution devices based at least in part on known contents of the stacked, machine manipulable containers stored therein.

Concept 16. The system of Concept 15 or any other Concept, in which the first location is a nursing station at a healthcare facility.

Concept 17. The system of Concept 16 or any other Concept, in which the second location is pharmacy.

Concept 18. The system of Concept 17 or any other Concept, further including a third storage and reconstitution device at a hazardous materials processing location.

Concept 19. The system of Concept 16 or any other Concept, in which the second location is a hazardous materials processing location.

Concept 20. The system of Concept 15 or any other Concept, in which the robotic components are further configured to: label the at least one of the plurality of stacked, machine-manipulable containers, and store tracking information for the at least one of the plurality of stacked, machine-manipulable containers.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

One or more aspects or features of the subject matter described herein may be realized in digital electronic circuitry, integrated circuitry, specially designed ASICs (application specific integrated circuits), computer hardware, firmware, software, and/or combinations thereof. For example, infusion pump systems disclosed herein may include an electronic system with one or more processors embedded therein or coupled thereto. Such an electronic system may include various types of computer readable media and interfaces for various other types of computer readable media. Electronic system may include a bus, processing unit(s), a system memory, a read-only memory (ROM), a permanent storage device, an input device interface, an output device interface, and a network interface, for example.

Bus may collectively represent all system, peripheral, and chipset buses that communicatively connect the numerous internal devices of electronic system of an infusion pump system. For instance, bus may communicatively connect processing unit(s) with ROM, system memory, and permanent storage device. From these various memory units, processing unit(s) may retrieve instructions to execute and data to process in order to execute various processes. The processing unit(s) can be a single processor or a multi-core processor in different implementations.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A storage and reconstitution device, comprising:
   a storage region configured to store a stack of machine-manipulable containers, each container including at least one crystalline hydration chemical;
   a sterile fluid reservoir; and
   robotic components configured to:
      move at least one container of the stack of machine-manipulable containers from the storage region to a connector fluidly coupled to the sterile fluid reservoir,
      add sterile fluid from the sterile fluid reservoir to the at least one container of the stack of machine-manipulable containers,
      agitate the at least one container of the stack of machine-manipulable containers,
      verify reconstitution of the at least one crystalline hydration chemical within the at least one container of the stack of machine-manipulable containers,
      label the at least one container of the stack of machine-manipulable containers, and
      store tracking information for the at least one container of the stack of machine-manipulable containers.

2. The storage and reconstitution device of claim 1, wherein each container of the stack of machine-manipulable containers includes a housing comprising a rigid portion and an expandable sealing membrane attached to the rigid portion to form a storage cavity therebetween for the least one crystalline hydration chemical and, wherein one or more container of the stack of machine-manipulable containers includes at least one crystalline therapeutic drug in the storage cavity thereof.

3. The storage and reconstitution device of claim 2, wherein the rigid portion of the housing of each container of the stack of machine-manipulable containers includes at least one feature engaged with a corresponding feature of an additional one container of the stack of machine-manipulable containers.

4. The storage and reconstitution device of claim 1, wherein the robotic components comprise a robotic arm configured to move the at least one container of the stack of machine-manipulable containers from the storage region to a connector fluidly coupled to the sterile fluid reservoir.

5. The storage and reconstitution device of claim 4, further comprising at least one pump configured to pump the sterile fluid from the sterile fluid reservoir to the at least one container of the stack of machine-manipulable containers.

6. The storage and reconstitution device of claim 5, wherein the robotic components further comprise an additional robotic arm configured to agitate the at least one container of the stack of machine-manipulable containers.

7. The storage and reconstitution device of claim 6, further comprising a labeler configured to generate the label on a rigid portion of the at least one container of the stack of machine-manipulable containers.

8. The storage and reconstitution device of claim 1, further comprising an optical component configured to verify reconstitution of the at least one crystalline hydration chemical within the at least one container of the stack of machine-manipulable containers.

9. The storage and reconstitution device of claim 8, wherein the optical component comprises a camera.

10. The storage and reconstitution device of claim 8, wherein the optical component comprises a laser verification device.

11. A system, comprising:
   a first storage and reconstitution device at a first location;
   a second storage and reconstitution device at a second location, wherein each of the first and second storage and reconstitution devices comprises:
      a storage region configured to store a stack of machine-manipulable containers, each container including at least one crystalline hydration chemical and at least one crystalline therapeutic drug;
a sterile fluid reservoir; and
robotic components configured to:
  move at least one container of the stack of machine-manipulable containers from the storage region to a connector fluidly coupled to the sterile fluid reservoir,
  add sterile fluid from the sterile fluid reservoir to the at least one container of the stack of machine-manipulable containers,
  agitate the at least one container of the stack of machine-manipulable containers, and
  verify reconstitution of the at least one crystalline hydration chemical and at least one crystalline therapeutic drug within the at least one container of the stack of machine-manipulable containers; and
a control system communicatively coupled via a network to the first and second storage and reconstitution devices and configured to push dose orders from clinicians to the first or second storage and reconstitution devices based at least in part on known contents of the stack of machine-manipulable containers stored therein.

12. The system of claim 11, wherein the first location is a nursing station at a healthcare facility.

13. The system of claim 12, wherein the second location is pharmacy.

14. The system of claim 13, further comprising a third storage and reconstitution device at a hazardous materials processing location.

15. The system of claim 12, wherein the second location is a hazardous materials processing location.

16. The system of claim 11, wherein the robotic components are further configured to:
  label the at least one container of the stack of machine-manipulable containers, and
  store tracking information for the at least one container of the stack of machine-manipulable containers.

17. The system of claim 11, wherein each container of the stack of machine-manipulable containers includes a housing comprising a rigid portion and an expandable sealing membrane attached to the rigid portion to form a storage cavity therebetween for the least one crystalline hydration chemical and, wherein one or more container of the stack of machine-manipulable containers includes at least one crystalline therapeutic drug in the storage cavity thereof.

18. The system of claim 17, wherein the rigid portion of the housing of each container of the stack of machine-manipulable containers includes at least one feature engaged with a corresponding feature of an additional one container of the stack of machine-manipulable containers.

19. The system of claim 11, wherein the robotic components comprise a robotic arm configured to move the at least one container of the stack of machine-manipulable containers from the storage region to a connector fluidly coupled to the sterile fluid reservoir.

20. The system of claim 19, further comprising at least one pump configured to pump the sterile fluid from the sterile fluid reservoir to the at least one container of the stack of machine-manipulable containers.

* * * * *